United States Patent [19]

Hermolin

[11] Patent Number: 4,482,746
[45] Date of Patent: Nov. 13, 1984

[54] STAGED CATALYST PROCESS FOR CYCLOHEXYL HYDROPEROXIDE DECOMPOSITION

[75] Inventor: Joshua Hermolin, Wilmington, Del.

[73] Assignee: E. I. Du Pont de Nemours & Company, Wilmington, Del.

[21] Appl. No.: 483,665

[22] Filed: Apr. 11, 1983

[51] Int. Cl.³ ............................................. C07C 45/53
[52] U.S. Cl. ..................................... 568/342; 568/835
[58] Field of Search ................................ 568/342, 835

[56] References Cited

U.S. PATENT DOCUMENTS

| | | | |
|---|---|---|---|
| 2,609,395 | 9/1952 | Dougherty et al. | 568/342 |
| 2,675,407 | 4/1954 | Gallo et al. | 568/342 |
| 2,851,496 | 9/1958 | Cates et al. | 568/342 |
| 3,093,686 | 6/1963 | Simon et al. | 568/342 |
| 3,404,185 | 10/1968 | Thomas et al. | 568/342 |
| 3,530,185 | 9/1970 | Pugi | 568/342 |
| 3,598,869 | 8/1971 | Volpe et al. | 568/342 |
| 3,855,307 | 12/1974 | Rony et al. | 568/342 |
| 3,917,708 | 11/1975 | Kuessner et al. | 568/342 |
| 3,923,895 | 12/1975 | Costantini et al. | 568/342 |
| 3,925,316 | 12/1975 | Brunie et al. | 568/342 |
| 3,927,105 | 12/1975 | Brunie et al. | 568/342 |
| 3,941,845 | 3/1976 | Voskuil et al. | 568/342 |
| 3,957,876 | 5/1976 | Rapoport et al. | 568/342 |
| 3,987,100 | 10/1976 | Barnette et al. | 568/342 |
| 3,987,101 | 10/1976 | Wolters et al. | 568/342 |
| 4,042,630 | 8/1977 | Wolters et al. | 568/342 |
| 4,326,084 | 4/1982 | Druliner et al. | 568/342 |
| 4,341,907 | 7/1982 | Zelonka | 568/342 |

Primary Examiner—James H. Reamer
Attorney, Agent, or Firm—Scott G. Hallquist

[57] ABSTRACT

An improvement in a process for decomposing cyclohexyl hydroperoxide to cyclohexanone and cyclohexanol is provided. According to the improved process, a reaction mixture comprising cyclohexane and cyclohexyl hydroperoxide is contacted with two catalyst compositions sequentially for a preselected reaction period, such that the reaction mixture is contacted with a catalytic amount of the first of said catalyst compositions only for about 10 to about 80 percent of the reaction period, and contacted with a catalytic amount of a mixture of the first and second catalyst compositions for the remainder of the preselected reaction time. The first catalyst composition of the invention is a cyclohexane-soluble chromium organic acid salt, and the second catalyst composition is a cobalt, iron, or manganese complex of a 1,3-bis(2-pyridylimino)isoindoline.

8 Claims, No Drawings

STAGED CATALYST PROCESS FOR CYCLOHEXYL HYDROPEROXIDE DECOMPOSITION

BACKGROUND OF THE INVENTION

This invention relates to an improved catalytic process for producing a mixture containing cyclohexanol and cyclohexanone. More particularly, the invention relates to a process wherein cyclohexyl hydroperoxide is decomposed in the presence of a staged binary catalyst system to produce a mixture containing cyclohexanol and cyclohexanone.

Industrial processes for producing mixtures of cyclohexanol and cyclohexanone from cyclohexane are currently of considerable commercial significance, and are well described in the patent literature. In accordance with typical industrial practice, cyclohexane is oxidized, forming a reaction mixture containing cyclohexyl hydroperoxide (CHHP). The resulting CHHP is decomposed, optionally in the presence of a catalyst, to form a reaction mixture containing cyclohexanol and cyclohexanone. In the industry, such a mixture is known as a K/A (ketone/alcohol) mixture, and can be readily oxidized to produce adipic acid, which is an important reactant in processes for preparing certain condensation polymers, notably polyamides. Due to the large volumes of adipic acid consumed in these and other processes, minor improvements in processes for producing adipic acid and its precursors can provide beneficial cost advantages.

Dougherty, et al., U.S. Pat. No. 2,609,395, disclose a process for oxidation of cycloalkanes to produce cycloalkanols and cycloalkanones, wherein a cycloalkane is reacted with limited quantities of oxygen. The cycloalkane hydroperoxides thus produced are decomposed by heating to a temperature between 150° C. and 210° C., in the presence of a cycloalkane, producing cycloalkanols and cycloalkanones.

Gallo, et al., U.S. Pat. No. 2,675,407, disclose optional use of polyvalent metal catalysts in a process for oxidizing cycloalkanes at a temperature between 100° C. and 200° C. Specific catalysts disclosed include finely divided metals such as cerium, cobalt, copper, manganese and vanadium, as well as inorganic and organic salts or oxides containing such metals.

Cates, et al., U.S. Pat. No. 2,851,496, disclose a process in which cyclohexane is oxidized with molecular oxygen, optionally in the presence of a catalyst, to provide a mixture containing cyclohexanol, cyclohexanone, and CHHP. According to this process, the resulting CHHP is subsequently decomposed to K and A by heating the mixture in the presence of a bed of solid decomposition catalyst. Catalysts disclosed by this reference include solid, granular metals or metal oxides, including iron, cobalt, nickel and oxides thereof, deposited upon inert supports.

Simon, et al., U.S. Pat. No. 3,093,686, disclose a process for oxidation of cyclohexane to produce mixtures of cyclohexanol and cyclohexanone, wherein oxidation is conducted in the presence of organic acid salts of cobalt, lead, manganese or chromium, which are added to a reactor as solutions in cyclohexane.

Brunie, et al., U.S. Pat. No. 3,925,316, disclose a method of catalytically decomposing CHHP comprising heating a mixture of CHHP and cyclohexane in the presence of a soluble organic salt or chelated derivative of vanadium, molybdenum, or ruthenium.

Kuessner, et al., U.S. Pat. No. 3,917,708, disclose a process for oxidizing cycloalkanes in the presence of heavy metal salt oxidation catalysts. The anions of the heavy metal salts can be monoalkylphosphate, dialkyl phosphate, monoalkyl sulfate, alkylsulfonic acid, alkylphosphonate or dialkylphosphonate.

Pugi, U.S. Pat. No. 3,530,185, discloses a process for oxidizing cyclohexane in which a mixture of gases containing oxygen is introduced to a cyclohexane stream. Optionally, a metal catalyst, in the form of a hydrocarbon-soluble compound, is added to the cyclohexane stream.

Rapoport, et al., U.S. Pat. No. 3,957,876, describe a process for oxidizing cyclohexane in which a cyclohexane-soluble cobalt salt is employed as catalyst. The cobalt salts disclosed include cobalt naphthenate, cobalt octoate, cobalt laurate, cobalt palmitate, cobalt stearate, cobalt linoleate and cobalt acetylacetonate.

The use of cyclohexane soluble complexes of chromium, e.g., chromium octoate and chromium naphthenate, as catalysts for CHHP decomposition is well known in the art. For example, Costantini, et al., U.S. Pat. No. 3,923,895, disclose a process for decomposing CHHP by heating a solution of CHHP and cyclohexane in the presence of a soluble chromium organic salt, which is added to a reactor column as a solution in cyclohexane. The Costantini patent also discloses that use of chromium salts as catalysts in CHHP decomposition can cause severe fouling of plant process equipment, since water produced in decomposition of CHHP to K deactivates and precipitates chromium ions from CHHP decomposition reaction mixtures.

Brunie, et al., U.S. Pat. No. 3,927,105, disclose a cascade CHHP decomposition process employing soluble chromium derivatives, including chromium carboxylates and chelated chromium derivatives, which are introduced, in solution, at the base of a reactor column. This patent also discloses that decomposition of CHHP catalyzed by soluble chromium complexes favors formation of K in preference to A with K/A ratios commonly in the range of 2.0 or greater. Brunie, et al., also disclose methods of removing water from CHHP decomposition mixtures to alleviate chromium fouling problems.

Wolters, et al., U.S. Pat. No. 3,987,101, disclose a process for producing cycloalkanones and cycloalkanols by decomposing cycloalkyl hydroperoxides in the presence of a solid chromium heterogenous catalyst.

Chromium complex catalysts are most efficient at reaction temperatures above 130° C. However, heating of CHHP solutions to temperatures above 130° C. results in significant uncatalyzed thermal decomposition of CHHP and lower yields of K and A. Certain transition metal catalysts, such as cobalt salts, can be used at lower temperatures, but produce lower K/A ratios, reducing yields of adipic acid in a subsequent nitric acid process in which mixtures of K and A are oxidized to produce adipic acid. One method of improving K/A ratios known in the art involves use of mixtures of soluble chromium and cobalt catalysts. For example, Barnette, et al., U.S. Pat. No. 3,987,100, disclose a process for oxidizing cyclohexane in the presence of a binary catalyst mixture comprising prescribed amounts of cyclohexane-soluble chromium and cobalt salts, at a temperature of from 130° C. to 200° C. CHHP formed during the reaction is decomposed to K and A in the presence of the binary catalyst.

Volpe, et al., U.S. Pat. No. 3,598,869, describe a process in which cyclohexane is oxidized to form nylon precursors, in the presence of oxygen and a soluble mixed cobalt and chromium binary catalyst. Reaction temperatures disclosed by this patent range from 135° C. to 180° C. The step in which cyclohexyl hydroperoxide is decomposed to cyclohexanone and cyclohexanol is not separately discussed.

Certain transition metal/ligand complexes are particularly useful catalyst compositions at lower temperatures. Druliner, et al., U.S. Pat. No. 4,326,084, disclose an improved catalytic process for oxidizing cyclohexane to form a reaction mixture containing CHHP, and for subsequently decomposing the resulting CHHP to form a mixture containing K and A, using certain transition metal complexes of 1,3-bis(pyridylimino)isoindolines. According to this patent, these catalysts demonstrate longer catalyst life, higher CHHP conversion to K and A, operability at lower temperatures (80°-160° C.), and reduced formation of insoluble metal-containing solids, relative to results obtained with certain cobalt(II) fatty acid salts, e.g., cobalt 2-ethylhexanoate.

Thus, cobalt and chromium CHHP decomposition catalysts exhibit differing patterns of inherent advantages and limitations. Accordingly, workers in the art have either tailored CHHP decomposition processes to particular requirements of either a chromium or a transition metal catalyst, or attempted CHHP decomposition using a binary mixture of chromium and transition metal catalysts. However, it can be demonstrated that a cobalt catalyst component dominates CHHP decomposition in a simple binary mixture, minimizing the advantages of adding a chromium component. For these reasons, a CHHP decomposition process which allows the advantages and limitations of each catalyst type to be balanced in a complementary fashion is desirable.

SUMMARY OF THE INVENTION

The present invention provides an improvement in a process for decomposing cyclohexyl hydroperoxide (CHHP) to produce cyclohexanone and cyclohexanol. According to the invention, a reaction mixture comprising cyclohexane and CHHP is contacted, at a temperature from about 80° C. to about 130° C. and at a pressure from about 69 kPa to about 2760 kPa, with two catalyst compositions sequentially for a preselected reaction period, such that the reaction mixture is contacted with a catalytic amount of the first of said catalyst compositions only for about 10 to about 80 percent of the reaction period, and contacted with a catalytic amount of a mixture of the first and second catalyst compositions for the remainder of the preselected reaction period, wherein the first catalyst composition consists essentially of a cyclohexane-soluble chromium (III) salt of an organic acid selected from the group consisting of 2-ethylhexanoic acid, naphthenic acids, lauric acid, stearic acid, palmitic acid, linoleic acid, certain monoalkylarene and dialkylarene sulfonic acids, or certain monoalkyl or dialkyl phosphoric acids or mixtures thereof, and the second catalyst composition consists essentially of one or more transition metal complexes having the structural formula

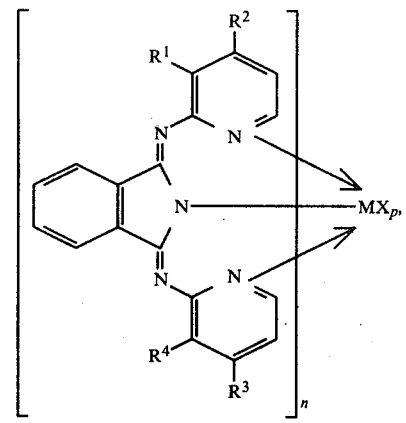

wherein the primary ligand is the entity in brackets;
M is Co, Mn or Fe;
$R^1$, $R^2$, $R^3$ and $R^4$ are independently hydrogen or methyl;
X is an ancillary anionic ligand;
n is 1 or 2; and
p is 0, 1 or 2, provided that n+p is 2 or 3; with the proviso that when there are two primary ligands, the values of $R^1$, $R^2$, $R^3$ and $R^4$ can be different for each ligand and when there are two ancillary anionic ligands, the value of X can be different.

DETAILED DESCRIPTION OF THE INVENTION

The present invention provides an improved process for conducting a cyclohexyl hydroperoxide (CHHP) decomposition step in an industrial process in which cyclohexane is oxidized to form a mixture containing cyclohexanol (A) and cyclohexanone (K). This industrial process involves two steps: first, cyclohexane is oxidized, forming a reaction mixture containing CHHP; second, CHHP is decomposed, forming a mixture containing K and A. As previously mentioned, processes for oxidation of cyclohexane are well described in the literature. Except for specific details described herein, cyclohexane oxidation and CHHP decomposition are to be conducted as described in the literature.

The improved CHHP decomposition process of the present invention, in which a reaction mixture containing CHHP is contacted with a staged catalyst system, provides several advantages. First, quantities of catalyst required for complete CHHP decomposition are minimized, thereby reducing fouling of plant process equipment and certain associated operating costs. Second, overall yields of K and A are improved by operation at lower temperatures. Third, K/A ratios are increased, resulting in higher adipic acid yields in later process steps. Fourth, yields of less desirable products, such as dicyclohexyl peroxide (DCHP), are reduced. Formation of reduced amounts of DCHP is desirable, since DCHP is converted to adipic acid in lower yield than K or A. The benefits of operation at lower temperatures, including increased CHHP decomposition efficiency, increased K/A ratios, and reduced DCHP formation, are maximized by sequential addition of a chromium organic salt catalyst composition followed by addition of a transition metal catalyst composition, such as a Co, Fe, or Mn complex of a 1,3-bis(2-pyridylimino)isoindoline. Simultaneous addition of these catalyst compositions, or addition in the reverse order, results in reduced CHHP decomposition efficiency, lower K/A ratios, and increased DCHP formation.

1. Catalyst Preparation and Use

The first catalyst composition of the staged catalytic process of the invention is a chromium organic acid salt soluble in cyclohexane. Preferred chromium compounds include chromium (III) salts of 2-ethylhexanoic acid (chromium octoate), napthenic acids (chromium naphthenate), alkylbenzene sulfonic acid, dialkylnaphthalene sulfonic acid, or dialkyl phosphoric acids, e.g., bis(2-ethylhexyl)phosphoric acid. Other suitable chromium salts include chromium laurate, chromium stearate, chromium palmitate and chromium linoleate. Other chromium organic salts which are known in the art as useful CHHP decomposition catalysts can also be employed in the process of the invention. For cost considerations, chromium octoate and chromium naphthenate are especially preferred.

The chromium salt can be added to a batch, semi-batch, or continuous CHHP decomposition reactor, at a concentration of chromium ion of from about 0.1 to about 30 parts per million (ppm), based upon the total reaction mixture. A preferred concentration for the chromium catalyst composition is from about 0.1 to about 10 ppm. In a continuous-flow operation, the chromium catalyst composition can be injected into the process stream at a point upstream from a point at which the second component of the staged catalyst system of the invention is injected.

The CHHP decomposition process stream or reaction mixture is contacted with the chromium salt catalyst composition for about 10 to about 80 percent of a preselected reaction period, which can vary, depending upon process variables, from about 3 to 30 minutes. Preferably, the time of contact is controlled such that the CHHP is permitted to decompose in contact with the chromium catalyst for about 30 to about 70 percent of the total reaction period before the second catalyst is injected into the reaction mixture or process stream.

The second catalyst composition of the invention has been previously described in detail in Druliner, et al., U.S. Pat. No. 4,326,084. Suitable transition-metal/ligand complexes for use as the second catalyst composition of the invention are transition metal complexes having the structural formula

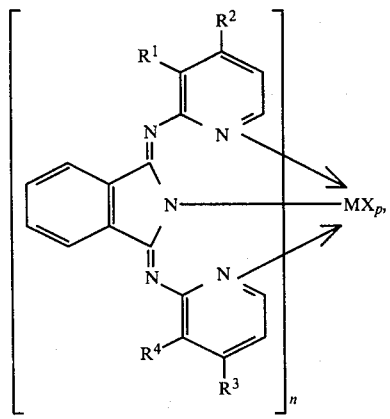

wherein the primary ligand is the entity in brackets;
M is Co, Mn or Fe;

$R^1$, $R^2$, $R^3$ and $R^4$ are independently hydrogen or methyl;

X is an ancillary anionic ligand;

n is 1 or 2; and p is 0, 1 or 2, provided that n+p is 2 or 3; with the proviso that when there are two primary ligands, the values of $R^1$, $R^2$, $R^3$ and $R^4$ can be different for each ligand and when there are two ancillary anionic ligands, the value of X can be different.

The following table sets forth examples of preferred transition metal/ligand complexes for use as the second catalyst composition of the invention:

| $R^1$ | $R^2$ | $R^3$ | $R^4$ | M | Designation |
|---|---|---|---|---|---|
| H | H | H | H | Co | Co(II)/1,3-bis(2-pyridylimino)-isoindoline |
| CH$_3$ | CH$_3$ | CH$_3$ | CH$_3$ | Co | Co(II)/1,3-bis(3,4-dimethyl-2-pyridylimino)isoindoline |
| CH$_3$ | H | H | CH$_3$ | Co | Co(II)/1,3-bis(3-methyl-2-pyridylimino)isoindoline |
| H | CH$_3$ | CH$_3$ | H | Co | Co(II)/1,3-bis(4-methyl-2-pyridylimino)isoindoline |
| CH$_3$ | H | CH$_3$ | H | Co | Co(II)/1-(3-methyl-2-pyridylimino)-3-(4-methyl-2-pyridylimino)isoindoline |

The most preferred catalyst, because of availability and activity, is the cobalt (II) derivative of 1,3-bis(3-methyl-2-pyridylimino)isoindoline (Co(3MeBPI)$_2$).

1,3-bis(2-pyridylimino)isoindolines can be prepared by the methods of Siegl, J. Org. Chem., 42 (11): 1872 (1977). For purposes of the present invention, 1,3-bis(2-pyridylimino)isoindolines can be prepared by using calcium chloride in the method described in the section entitled "General Preparation . . . Using Alkaline Earth Salts" (page 1877 of the Siegl article). Stable dispersions of transition metal/1,3-bis(2-pyridylimino)isoindoline complexes can be prepared at ambient conditions by mixing a metal carboxylate with a 1,3-bis(2-pyridylimino)isoindoline in K or A.

The ancillary anionic ligand, X, can be selected from various possibilities which include carboxylate groups, such as acetate, propionate, 2-ethylhexanoate, gluconate, and naphthenate; an anion of any other organic acid; hydroxide and μ-oxide (O$^{-2}$/2); dialkyl phosphate, or alkyl or alkaryl sulfonate. The nature of the ancillary anionic ligand has little direct effect on catalyst activity but can affect solubility, thereby indirectly affecting activity.

The concentration of the second catalyst composition in the staged catalyst system of the invention, measured as the concentration of metal cation added to the total process mixture, can be from about 0.1 to about 30 ppm, and preferably ranges from about 0.1 to about 10 ppm. Typically, lower catalyst concentrations are required at higher temperatures.

2. Process Variables

Since CHHP is typically produced industrially as a solution in cyclohexane from catalytic oxidation of cyclohexane, a convenient and preferred solvent for the CHHP decomposition process of the invention is cyclohexane. Such a mixture can be used as received from the first step of the cyclohexane oxidation process or after some of the constituents have been removed by known processes. To minimize fouling of process equipment, the effluent from the cyclohexane oxidation process is preferably water-washed, using known techniques, prior to CHHP decomposition.

The concentration of CHHP in the CHHP decomposition mixture can range from about 0.1% to about 10% by weight, preferably from about 0.5% to about 3% by weight.

Duration of the preselected reaction period depends upon temperature and catalyst concentration and typically ranges from about 5 to about 30 minutes. Longer periods can be used, but usually no advantage results. Reaction temperatures for the CHHP decomposition process of the present invention are from about 80° C. to about 130° C. A preferred temperature range is from about 110° to about 125° C. Pressures from about 69 to about 2760 kPa (10–400 psi) gauge pressure are suitable, and pressures from about 276 to about 1380 kPa (40–200 psi) are preferred.

The relative percentage of the preselected reaction period during which the reaction mixture is contacted with the first catalyst composition only can be varied, depending upon the composition of the reaction mixture, from about 10 to 80 percent of the total reaction period. The optimal contact period for a given set of reaction conditions can be determined empirically, by contacting the mixture to be decomposed with a chromium-containing catalyst chosen as the first catalyst composition of the invention for a preselected period, terminating the reaction, and measuring the extent of CHHP decomposition by GC or other means.

In general, the optimal period for contact with the chromium-containing catalyst composition will be determined by such factors as reaction temperature and reaction mixture composition. As noted previously, chromium-containing catalysts are more active at higher temperatures. In addition, water and certain low molecular weight carboxylic acids, which can be present in CHHP decomposition mixtures, deactivate chromium-containing catalysts. Also, chromium-containing CHHP decomposition catalysts are less efficient at very low CHHP concentrations.

Thus, where water, low molecular weight carboxylic acids, or other chromium-deactivating components are present in a given CHHP decomposition mixture, or CHHP concentrations are low (<0.3% by weight), the time of contact with a mixture of the first and second catalyst compositions of the staged catalyst system of the invention can be increased to reduce residual CHHP to a minimum.

On the other hand, where CHHP concentrations are relatively high (>0.5% by weight), and concentrations of water and other chromium-deactivating materials in a given reaction mixture are relatively low, the time of contact with the first catalyst composition of the invention can be increased, to take advantage of the improved product distributions obtainable with chromium-containing catalysts, relative to cobalt-containing catalysts.

The invention is further illustrated by the following examples in which all temperatures are in degrees Celsius and all percentages are by GC area percent unless otherwise specified.

EXAMPLES

Comparisons A–F and Examples 1 and 2 record the results of a series of experiments in which the staged catalyst system of the present invention was evaluated in a laboratory-scale pulse reactor. In addition, the staged catalyst system was compared to single catalysts representative of the prior art. Each of these experiments was performed using substantially similar methods, and the apparatus and procedures used are detailed below.

Apparatus

The apparatus used in these experiments was a stainless-steel pulse reactor having a volume of about 125 ml and usable at internal pressures up to about 2070 kPa (300 psi) gauge pressure. The reactor had a pressure-relief valve to insure that allowable pressure was not exceeded and was equipped with a side-arm with a septum for injection of liquid from a hypodermic syringe. Liquid contents (typically about 25 ml) in the apparatus could be stirred by an external magnetic drive. Heating was provided by partial immersion in a fluidized bed regulated by a proportional heater control. Temperatures were measured with a platinum resistance thermometer using digital temperature display and analog output.

Procedure

The reactor was charged with 25 ml cyclohexane for each experiment and sealed. The reactor head was warmed to about 130° over a period of about ten minutes, using a heating tape affixed to the top of the reactor. At this point, the reactor was placed in a fluidized bed heater, which had previously been heated to about 115°. The reactor and its contents were permitted to equilibrate, with stirring, at the fluidized bed temperature for about 10 minutes.

At this point, 2.25 ml of a concentrated, water-washed air oxidizer tails solution (W/W A/O tails) was injected into the reactor. "W/W A/O tails" is the designation given to an effluent from a plant cyclohexane air oxidizer, which has been water-washed prior to further processing, for example, in a CHHP decomposition reactor. For purposes of the experiments set forth in the Examples and Comparisons, the effluent of a plant air oxidizer was extracted by washing about one part A/O tails with about 0.33 parts water in a glass separatory funnel for about ten minutes. An aqueous phase was permitted to separate on standing for about 15 minutes and discarded. The remaining cyclohexane phase was concentrated by evaporation in a rotary evaporator at about 60–80 mm Hg vacuum at 25°±2° until the cyclohexane phase had been concentrated by a factor of about 12.

Immediately after injection of the W/W A/O tails solution containing CHHP, the first catalyst component to be employed in a given experiment was injected into the pulse reactor. The second catalyst was injected after a period of from about 0 to about 10 minutes later, and the reaction permitted to proceed for a total period of about 20 minutes in each case. At the end of a given experiment, the reactor was quickly cooled by immersion in an ambient temperature water bath. The reactor was then opened, and its contents analyzed by GC to determine relative concentrations of K, A, CHHP and DCHP. Experimental conditions for the Examples and Comparisons were selected to simulate, as closely as practicable, the conditions under which CHHP is decomposed on an industrial scale.

The results of these experiments are set forth in Table 1, below. The relative concentrations of K, A, CHHP, and DCHP in a representative sample of the contents of the reactor at the start of a given experiment appear in the first row of results in Table 1. In Table 1, concentrations of catalyst compositions are provided in parts per million (ppm), by weight, measured as the concentration of metal in the total reaction mixture. The designation "Cr" in Table 1 indicates that a solution of chromium(III)ethylhexanoate was used in that example. The designation "Co" indicates that a cobalt(II) derivative of 1,3-bis(3-methyl-2-pyridylimino)isoindoline was used as catalyst. The times listed under the column marked "Delay" represent the duration of the period during which the reactor contents were stirred in contact with the first catalyst only.

TABLE 1

CHHP Decomposition Experiments Employing Staged Addition of Chromium and Cobalt/Ligand Catalysts

| Example | Catalyst (ppm) First | Catalyst (ppm) Second | Delay (min) | GC Analysis (Area %) CHHP | GC Analysis (Area %) DCHP | GC Analysis (Area %) A | GC Analysis (Area %) K | K/A Ratio |
|---|---|---|---|---|---|---|---|---|
| Starting Solution | — | — | — | 0.988 | 0.023 | 1.363 | 0.642 | 0.47 |
| A | None added | — | — | 0.715 | 0.020 | 1.501 | 0.927 | 0.62 |
| B | 1.0 Co | — | — | 0.044 | 0.080 | 2.102 | 0.907 | 0.43 |
| C | 5.0 Cr | — | — | 0.041 | 0.027 | 1.799 | 1.499 | 0.83 |
| D | 1.0 Cr | — | — | 0.301 | 0.022 | 1.624 | 1.152 | 0.71 |
| E | 0.5 Co | 1.0 Cr | 5 | 0.057 | 0.047 | 1.865 | 0.831 | 0.44 |
| 1 | 1.0 Cr | 0.5 Co | 5 | 0.036 | 0.045 | 1.752 | 1.001 | 0.57 |
| 2 | 0.5 Cr | 0.5 Co | 10 | 0.136 | 0.040 | 1.754 | 1.057 | 0.60 |
| F | 1.0 Cr | 0.5 Co | 0 | 0.033 | 0.052 | 2.113 | 0.933 | 0.44 |

DISCUSSION OF EXPERIMENTAL RESULTS

Comparison A

Comparison A indicates that only 28% of starting CHHP was decomposed in the absence of catalysts under the reaction conditions detailed above.

Comparison B

Comparison B demonstrates that 1 ppm cobalt, in the form of a cobalt(II) derivative of 1,3-bis(3-methyl-2-pyridylimino)isoindoline (Co(3MeBPI)$_2$), catalyzed decomposition of about 96% of the starting CHHP. A relatively low K/A ratio of 0.43 and an approximate three-fold increase in DCHP concentration are characteristic of cobalt-catalyzed CHHP decomposition reactions.

Comparisons C and D

Comparison C shows that 5 ppm chromium catalyzed decomposition of 96% of starting CHHP. A relatively high K/A ratio of 0.83 and a low level of DCHP formation are characteristic of chromium-catalyzed CHHP decomposition reactions. Comparison D indicates that 1 ppm chromium catalyzed the decomposition of about 70% of the starting CHHP.

Comparison E

Comparison E demonstrates that injection of 0.5 ppm cobalt, followed five minutes later by injection of 1 ppm chromium, provided less CHHP decomposition and a lower K/A ratio (0.44) than that obtained with the preferred order of catalyst injections exemplified by Examples 1 and 2, below.

EXAMPLE 1

Example 1 shows that stepwise injection of 1 ppm chromium, followed 5 minutes later by 0.5 ppm cobalt, resulted in efficient decomposition of starting CHHP, a moderate increase in DCHP concentration, and a K/A product ratio of 0.57.

EXAMPLE 2

Example 2 demonstrates that the concentrations of chromium and cobalt catalysts, as well as the time of catalyst injection, can be varied. Similar K/A ratios and DCHP concentrations were obtained in Example 2 and Example 1, with comparably high levels of CHHP decomposition in Example 2 (86%) and Example 1 (96%).

Comparison F

Comparison F shows that simultaneous injection of chromium and cobalt catalysts provided results inferior to those obtained in the experiments illustrated by Examples 1 and 2. Specifically, the K/A ratio of Comparison F was significantly lower than the product K/A ratios observed in Examples 1 and 2.

I claim:

1. In a process in which cyclohexyl hydroperoxide is decomposed in a reaction mixture comprising cyclohexyl hydroperoxide and cyclohexane to produce cyclohexanone and cyclohexanol, the improvement comprising contacting the reaction mixture, at a temperature from about 80° C. to about 130° C. and at a pressure from about 69 kPa to about 2760 kPa, with two catalyst compositions sequentially for a preselected reaction period, such that the reaction mixture is contacted with a catalytic amount of the first of said catalyst compositions only for about 10 to about 80 percent of the reaction period, and contacted with a catalytic amount of a mixture of the first and second catalyst compositions for the remainder of the preselected reaction time, wherein the first catalyst composition consists essentially of a cyclohexane-soluble chromium(III) salt of an organic acid selected from the group consisting of 2-ethylhexanoic acid, naphthenic acids, monoalkylarene or dialkylarene sulfonic acids, monoalkyl or dialkyl phosphoric acids or mixtures thereof, lauric acid, stearic acid, palmitic acid or linoleic acid, and the second catalyst composition consists essentially of one or more transition metal complexes having the structural formula

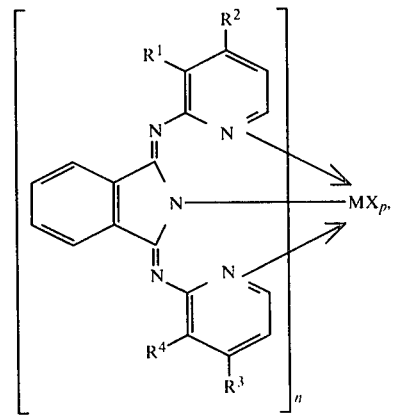

wherein the primary ligand is the entity in brackets; M is Co, Mn or Fe;

$R^1$, $R^2$, $R^3$ and $R^4$ are independently hydrogen or methyl;

X is an ancillary anionic ligand;

n is 1 or 2; and p is 0, 1 or 2, provided that n+p is 2 or 3; with the proviso that when there are two primary ligands, the values of $R^1$, $R^2$, $R^3$ and $R^4$ can be different for each ligand and when there are two ancillary anionic ligands, the value of X can be different.

2. A process according to claim 1, wherein the temperature is from about 110° C. to about 125° C., and the pressure is from about 276 kPa to about 1380 kPa.

3. A process according to claim 2, wherein the reaction mixture contains from about 0.1 to about 10 percent by weight cyclohexyl hydroperoxide.

4. A process according to claim 3, wherein each catalyst composition is added to the reaction mixture to a final concentration, measured as a concentration of each metal cation in the reaction mixture, of from about 0.1 to about 30 ppm by weight.

5. A process according to claim 4, wherein each catalyst composition is added to the reaction mixture to a final concentration, measured as a concentration of each metal cation in the reaction mixture, of from about 0.1 to about 10 ppm by weight.

6. A process according to claim 5, wherein the reaction mixture is contacted with the first catalyst composition only for about 30 to about 70 percent of the preselected reaction period.

7. A process according to claim 6, wherein the first catalyst composition is a chromium(III) salt of a naphthenic acid, 2-ethylhexanoic acid, dialkylnaphthalene sulfonic acid, alkylbenzene sulfonic acid, or bis(2-ethylhexyl)phosphoric acid, and the second catalyst composition is a cobalt(II) derivative of
1,3-bis(3-methyl-2-pyridylimino)isoindoline,
1,3-bis(4-methyl-2-pyridylimino)isoindoline,
1,3-bis(2-pyridylimino)isoindoline,
1-(3-methyl-2-pyridylimino)-3-(4-methyl-2-pyridylimino)isoindoline, or
1,3-bis(3,4-dimethyl-2-pyridylimino)isoindoline.

8. A process according to claim 7, wherein the first catalyst composition is a chromium(III) salt of 2-ethylhexanoic acid, and the second catalyst composition is a cobalt(II) derivative of 1,3-bis(3-methyl-2-pyridylimino)isoindoline.

* * * * *